United States Patent [19]

Naieni

[11] Patent Number: 5,709,774
[45] Date of Patent: Jan. 20, 1998

[54] HEAT TREATED HIGH LIGNIN CONTENT CELLULOSIC FIBERS

[75] Inventor: Shahrokh A. Naieni, Cincinnati, Ohio

[73] Assignee: The Procter & Gamble Company, Cincinnati, Ohio

[21] Appl. No.: 638,463

[22] Filed: Apr. 26, 1996

Related U.S. Application Data

[63] Continuation of Ser. No. 218,797, Mar. 24, 1994, abandoned.

[51] Int. Cl.$^6$ .................................................. D21C 9/00
[52] U.S. Cl. ........................... 162/9; 162/65; 162/100; 162/142
[58] Field of Search .................. 162/9, 23, 28, 162/63, 65, 100, 19, 141, 142, 149

[56] References Cited

U.S. PATENT DOCUMENTS

| | | | |
|---|---|---|---|
| 3,256,614 | 6/1966 | Dunbar | 162/100 |
| 4,036,679 | 7/1977 | Back et al. | 162/9 |
| 4,065,347 | 12/1977 | Aberg et al. | 162/100 |
| 4,081,316 | 3/1978 | Aberg et al. | 162/100 |
| 4,343,680 | 8/1982 | Field et al. | 162/100 |
| 4,431,479 | 2/1984 | Barbe et al. | 162/9 |
| 4,455,237 | 6/1984 | Kinsley | 162/146 |
| 4,557,800 | 12/1985 | Kinsley, Jr. | 162/20 |
| 4,752,354 | 6/1988 | Beurich et al. | 162/72 |

FOREIGN PATENT DOCUMENTS

| | | | |
|---|---|---|---|
| 232954 | 2/1961 | Australia | 162/100 |
| 1367670 | 9/1974 | United Kingdom | 162/100 |

OTHER PUBLICATIONS

Hart, J.R., "Chelating Agents in the Pulp and Paper Industry"; Sep. 1981, ABIPC 52:3, p. 304–305.

Levina, R.R., "Influence of Heat Treatment on Fiber Structure of Thermochemical Pulp from Aspen"; Mar. 1984, ABIPC 54:9, p. 1043.

Gellerstedt, G., "Improved Brightness of CTMP by Defibration in Presence of Sodium Sulfite and DTPA"; Apr. 1984, ABIPC 54:10, p. 1163.

Mohlin, U.B., "Tailoring CTMP Pulps to Meet Specific End–Uses"; Aug. 1987, ABIPC 58:2, p. 232.

Daneault, Kokta, Maldas, "Grafting of Vinyl Monomers onto Wood Fibers Initiated by Peroxidation", Feb. 1989, ABIPC 59:8, p. 865.

English Abstract No. 74960A/42, Patent No. J5 3103–002, Sep. 7, 1978.

English Abstract No. 44891B/24, Patent No. J5 4055–607, May 2, 1979.

English Abstract No. 84–153716/25, Patent No. DE 3344–865–A, Jun. 14, 1984.

English Abstract No. 89–292546/40, Patent No. WO 8908–738–A, Sep. 21, 1989.

Mohlin, "Tailoring CTMP Pulps to Meet Specific End–Uses," *Paper* (London) 207(7):22–24 (1987).

*Primary Examiner*—Peter Chin
*Attorney, Agent, or Firm*—Harness, Dickey & Pierce, P.L.C.

[57] ABSTRACT

Heat-treated-in-air high lignin content cellulosic fibers which are free of moieties from crosslinking agents, for use in absorbent structures, are prepared by fluffing high lignin content fibers at a consistency of at least 40%, and heating in air at atmospheric pressure at a temperature ranging from 120° C. to 280° C. fluffed fiber water admixture having a consistency of at least 60% or moisture-free fluffed fibers, to remove any moisture content and heat treat the resulting moisture-free high lignin content fibers for at least 5 seconds, or by heating a sheet of dry (0–40% moisture content) high lignin content fibers utilizing these same heating conditions and then fluffing.

9 Claims, No Drawings

HEAT TREATED HIGH LIGNIN CONTENT CELLULOSIC FIBERS

This is a continuation of U.S. patent application Ser. No. 08/218,797, filed Mar. 24, 1994, now abandoned.

TECHNICAL FIELD

This invention is directed to modified high lignin content cellulosic fibers, to absorbent structures containing these fibers, and to methods for modifying high lignin content cellulosic fibers for use in absorbent structures.

BACKGROUND OF THE INVENTION

High lignin cellulosic fibers have the advantages of being inexpensive and relatively chemical-free compared to fibers from bleached Kraft pulp. However, they are not useful as major constituents in absorbent structures, e.g., diapers and catamenial products, because of their high hydrophobicity due to the presence of such a large amount of hydrophobic lignin.

The patent application of S. A. Naieni and C. M. Herron, entitled "Esterified High Lignin Content Cellulosic Fibers" filed concurrently herewith, is directed to modifying high lignin content cellulosic fibers with intrafiber $C_2$-$C_9$ polycarboxylic acid ester moieties, for use in absorbent structures.

Kinsley, Jr., U.S. Pat. No. 4,557,800 is directed to thermally treating cellulosic pulps in a non-oxidizing gaseous medium at a temperature exceeding about 400° F. to provide a pulp without loss of hemicellulose.

Barbe et al U.S. Pat. No. 4,431,479 is directed to subjecting mechanical, ultra high-yield or high yield pulps to mechanical action at high consistency (15–35%) to make the fibers curly and subjecting the curled pulp at high consistency (say 15–35%) to heat treatment at high pressures without appreciable drying of the pulp.

SUMMARY OF THE INVENTION

It has been discovered herein that heat-treated-in-air high lignin content cellulosic fibers which are free of moieties from crosslinking agents perform unexpectedly well in absorbent applications.

One embodiment herein is directed to heat-treated-in-air high lignin content cellulosic fibers which are free of moieties from crosslinking agents and have a water retention value ranging from 90 to 135 and a dry resiliency defined by a density after pressing (i.e., a 5K density) ranging from 0.10 to 0.20 g/cc. In practice, often the fibers have a water retention value ranging from 110 to 125, a dry resiliency defined by a 5K density ranging from 0.12 to 0.18 g/cc, a wet resiliency defined by a wet compressibility ranging from about 7.2 to 8.2 cc/g and a drip capacity ranging from about 5.5 to 12.0 g/g.

A second embodiment herein is directed to an absorbent structure comprising said heat-treated-in-air high lignin content cellulosic fibers.

A third embodiment herein is directed to a method for preparing the heat-treated-in-air high lignin content cellulosic fibers which are free of moieties from crosslinking agents and have a water retention value ranging from 90 to 135 and a dry resiliency defined by a 5K density ranging from 0.08 to 0.20 g/cc and comprises the steps of (a) providing high lignin content cellulosic fibers at a consistency of 40 to 100%, which are free of admixture with crosslinking agent; (b) subjecting the fibers to defibration; and (c) heating in air at atmospheric pressure to remove any moisture content and heat treat the moisture-free high lignin content cellulosic fibers for at least 5 seconds, thereby to produce said heat-treated-in-air high lignin content cellulosic fibers. Preferably, the admixture of step (a) has a consistency ranging from 45 to 80%, very preferably from 50 to 70%. The heating of step (c) may be carried out in two stages, a first drying stage (e.g., flash drying) to obtain a consistency of at least 60% if this consistency is not already present or to increase the consistency if a consistency of at least 60% is already present, e.g., to 85–95% or even 100% consistency, and a second stage to remove any remaining moisture content and heat treat the moisture-free high lignin content cellulosic fibers, e.g., by heating for 5 seconds to 2 hours at an air temperature in the heating apparatus of 120° C. to 280° C., preferably for 2 to 75 minutes at an air temperature in the heating apparatus of 150° C. to 190° C.

A fourth embodiment herein is directed to a method for preparing the heat-treated-in-air high lignin content cellulosic fibers which are free of moieties from crosslinking agents and have a water retention value ranging from 90 to 135 and a dry resiliency defined by a 5K density ranging from 0.08 to 0.20 g/cc and comprises the step of heating a dry (0–40% moisture content) sheet of high lignin content cellulosic fibers in air at atmospheric pressure to remove any moisture content and heat treat the moisture-free high lignin content cellulosic fibers for at least 5 seconds, e.g., the step of heating for 5 seconds to 2 hours at an air temperature in the heating apparatus of 120° C. to 280° C., preferably heating for 2 minutes to 75 minutes at an air temperature in the heating apparatus of 150° C. to 190° C., and optionally the further step of defibrating.

The fibers resulting from the methods herein are optionally moisturized to protect them from damage in subsequent handling or in processing to make absorbent products.

The heat-treated-in-air high lignin content cellulosic fibers prepared as described above are ready for packaging or for use.

The term "high lignin content" is used herein to mean 10 to 25% by weight lignin, on a dry basis.

The "water retention values" (referred to in the Examples herein as WRV) set forth herein are determined herein by the following procedure: A sample of about 0.3 g to about 0.4 g of fibers (i.e., about a 0.3 g to about a 0.4 g portion of the fibers for which water retention values are being determined) is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value (WRV) is calculated as follows:

$$WRV = \frac{(W-D)}{D} \times 100$$

where,

W=wet weight of the centrifuged fibers;

D=dry weight of the fibers; and

W−D=weight of absorbed water.

The term "dry resiliency" is used herein to refer to the ability of a structure made from the fibers herein to expand upon release of compressional force applied while the fibers are in substantially dry condition. Dry resiliency defined by a density after pressing is a measure of fiber stiffness and is determined herein in the 5K density test according to the following procedure: A four inch by four inch square air laid pad having a mass of about 7.5 g is prepared from the fibers for which dry resiliency is being determined, and compressed, in a dry state, by a hydraulic press to a pressure of 5000 psi, and the pressure is quickly released. The pad is inverted and the pressing is repeated and released. The thickness of the pad is measured after pressing with a no-load caliper (Ames thickness tester). Five thickness readings are taken, one in the center and 0.001 inches in from each of the four corners and the five values are averaged. The pad is trimmed to 4 inches by 4 inches and then is weighed. Density after pressing is then calculated as mass/(area×thickness). This density is denoted the 5K density herein. The lower the 5K density, the greater the dry resiliency.

The term "wet resiliency" is used herein to refer to the ability of a structure to expand upon release of compressional forces while the fibers are moistened to saturation. The wet resiliency defined by a void volume after reduction of compression of load is a measure of wet void volume and is determined herein in the "wet compressibility test" by the following procedure: An air laid four inch by four inch square pad weighing about 7.5 g is prepared from the fibers being tested. The density of the pad is adjusted to 0.2 g/cc with a press. The pad is loaded with synthetic urine to ten times its dry weight or to its saturation point, whichever is less. A 0.1 PSI compressional load is applied to the pad. After about 60 seconds, during which time the pad equilibrates, the compressional load is then increased to 1.1 PSI. The pad is allowed to equilibrate, and the compressional load is then reduced to 0.1 PSI. The pad is then allowed to equilibrate, and the thickness is measured. The density is calculated for the pad at the second 0.1 PSI load, i.e., based on the thickness measurement after the pad equilibrates after the compressional load is reduced to 0.1 PSI. The void volume reported in cc/g, is then determined. The void volume is the reciprocal of the wet pad density minus the fiber volume (0.95 cc/g). This void volume is denoted the wet compressibility herein. Higher values indicate greater wet responsiveness.

The drip capacity test herein provides a combined measure of absorbent capacity and absorbency rate and is determined herein by the following procedure: A four inch by four inch square air laid pad having a mass of about 7.5 g is prepared from the fibers for which drip capacity is being determined and is placed on a screen mesh. Synthetic urine is applied to the center of the pad at a rate of 8 ml/s. The flow of synthetic urine is halted when the first drop of synthetic urine escapes from the bottom or sides of the pad. The drip capacity is calculated by the difference in mass of the pad prior to and subsequent to introduction of the synthetic urine divided by the mass of the fibers, bone dry basis. The greater the drip capacity is, the better the absorbency properties.

The term "synthetic urine" is used herein to mean solution prepared from tap water and 10 grams of sodium chloride per liter of tap water and 0.51 ml of a 1.0% aqueous solution of Triton X100 per liter of tap water. The synthetic urine should be at 25°±1° C. when it is used.

The terms "defibration" and "defibrating" are used herein to refer to any procedure which may be used to mechanically separate fibers into substantially individual form even though they are already in such form, i.e., to the step(s) of mechanically treating fibers in either individual form or in more compacted form, where the treating (a) separates the fibers into substantially individual form if they were not already in such form and/or (b) imparts curl to the fibers in dry state.

The term "the fibers herein" refers to heat-treated-in-air high lignin content cellulosic fibers which are free of moieties from crosslinking agents and which have a water retention value ranging from 90 to 135 and a dry resiliency defined by a density after pressing ranging from 0.08 to 0.20 g/cc.

The term "heat treat" is used herein to mean heating in the absence of moisture.

DETAILED DESCRIPTION

The high lignin content fibers modified herein can be of diverse origin. Preferably, the original source is softwood or hardwood. Other sources include esparto grass, bagasse, hemp and flax and other high lignin content cellulosic fiber sources.

The high lignin content fibers which are modified herein are, for example, chemithermomechanical pulps from the above sources, thermomechanical pulps from the above sources, and recycled fiber streams from Kraft bags and boxes where the fiber lignin content is 10% or more, on a dry basis. Unbleached cellulosic chemical pulps may also meet a 10–25% lignin content level and constitute high lignin content fibers which may be modified according to the invention herein. Chemithermomechanical pulps may be prepared in conventional fashion, e.g., by chemical treatment of source material pieces (e.g., wood chips) with, for example, sodium sulfite and/or sodium metabisulfate and a chelating agent, e.g., diethylenetriamine pentaacetic acid (DTPA), followed by processing through a disc refiner. Thermomechanical pulps may be prepared, in conventional fashion, for example, by steam treating (e.g., at conditions of 34 psi and 265° F. for 20 minutes) source material pieces (e.g., wood chips), and then processing the steam treated material through a disc refiner. Recycled fiber streams are obtained from recycled Kraft bags and boxes, e.g., by agitating them in water and then dewatering.

Northern softwood chemithermomechanical pulp is a preferred starting material since it is readily commercially available.

We turn now to the method of the third embodiment herein (i.e., the method comprising the steps of (a) providing high lignin content cellulosic fibers at a consistency of 40 to 100%, which are free of admixture with crosslinking agent; (b) subjecting the fibers to defibration; and (c) heating the product of step (b) in air at atmospheric pressure to remove any moisture content and heat treat the moisture-free high lignin content cellulosic fibers for at least 5 seconds.

We turn firstly to step (a) of the method of the third embodiment herein, i.e., the step of providing high lignin content cellulosic fibers at a consistency of 40 to 100% which are free of admixture with crosslinking agent.

This step is readily carried out for fibers in unrestrained condition or for fibers in sheet form.

For low moisture contents, i.e., 0 to about 10%, step (a) can simply involve assembling fibers in sheet form or unrestrained form which are obtained with this moisture content. For higher moisture contents, e.g., consistencies of about 40 to 90%, step (a) involves forming an admixture of the fibers and water.

The pH of the admixture can range, for example, from 2.5 to 9 and is a parameter which affects the dry resiliency, the wet resiliency and the drip capacity obtained in the modified fiber product (i.e., the result of step (c)). The dry resiliency (5K density) and wet resiliency (wet compressibility) values obtained are better when lower pHs, for example, 2.5 to 4.0, are used. The drip capacities are better when middle pHs, for example, 6.0 to 7.0, are used. The natural pH of the admixture is typically about 9. Adjustment of pH downward is readily carried out with acid, preferably sulfuric acid. Hydrochloric acid is preferably not used since it is preferred to obtain modified fibers which are chlorine-free.

Uniform consistency and uniform distribution of any pH adjusting additive is readily obtained for a sheet of fibers, e.g., by transporting the sheet of fibers (e.g., initially at 0 to 10% moisture content) through a body of aqueous composition comprising water and any pH adjusting agent, contained in a nip of press rolls (e.g., rolls 1 foot in diameter and 6 feet wide) and through said nip to impregnate the sheet of fibers with the aqueous composition and to produce on the outlet side of the nip an impregnated sheet of fibers containing the aqueous composition in an amount providing a consistency of 30 to 80% or more (e.g., even up to 85% or 90% or even 95%), preferably a consistency of 50 to 70%. In a less preferred alternative, the sheet of fibers is impregnated with aqueous composition to provide the aforementioned consistencies by spraying. In either case, if the consistency is less than the 40% lower limit for step (a), liquid removal is carried out to obtain the at least 40% consistency lower limit, and even if the consistency is 40% or more, liquid removal is optionally carried out to raise the consistency, e.g., by dewatering (i.e., mechanically removing liquid, e.g., by centrifuging or pressing) and/or by drying under conditions such that utilization of high temperature for an extended period of time is not required, e.g., by a method known in the art as air drying. For example, a sheet of fibers at a moisture content of 6% can be passed through the body of aqueous composition and press rolls to produce an impregnated sheet of fibers of 60% consistency or 80% consistency which is ready for treatment in step (b) or to produce an impregnated sheet of fibers of a consistency of 40% which is optionally subjected to a liquid removal step or steps as described above, e.g., to provide a consistency of 60%, before treatment in step (b).

Uniform consistency and uniform distribution of any pH adjusting additive is readily obtained for fibers in unrestrained form, e.g., by soaking fibers in unrestrained form in a body of said aqueous composition.

The soaking is readily carried out, e.g., by forming a slurry of fibers in unrestrained form in water, with pH adjustment, if desired, to provide a consistency ranging from 0.1 to 20%, preferably ranging from 2 to 15%, and maintaining them therein for about 1 to 240 minutes, preferably for 5 to 60 minutes. Forming a slurry of fibers in unrestrained form in water is readily carried out either by admixing fibers in unrestrained form with water or by causing a sheet of the fibers (e.g., drylap) to disintegrate in the water.

At the consistencies of 0.1 to 20%, one or more liquid removal and/or drying steps are required to provide the consistencies of 40 to 100% recited for step (a). Preferably, these comprise dewatering (i.e., mechanically removing liquid, e.g., by centrifuging or pressing) to provide a consistency between 40 and 80%, for example, 40 to 50%, and optionally thereafter drying further under conditions such that utilization of a high temperature for an extended period of time is not required, e.g., by a method known in the art as air drying, to a consistency of 50 to 80% or even up to 100%, preferably to a consistency ranging from 50 to 70%.

We turn now to step (b) of the method of the third embodiment herein, i.e., the step of subjecting the fibers from step (a) to defibration, sometimes referred to as fluffing. Defibration is preferably performed by a method wherein knot and pill formation and fiber damage are minimized. Typically, a commercially available disc refiner is used. Another type of device which has been found to be particularly useful for defibrating the cellulosic fibers is the three stage fluffing device described in U.S. Pat. No. 3,987,968, issued to D. R. Moore and O. A. Shields on Oct. 26, 1976, said patent being hereby expressly incorporated by reference into this disclosure. The fluffing device described in U.S. Pat. No. 3,987,968 subjects moist cellulosic pulp fibers to a combination of mechanical impact, mechanical agitation, air agitation and a limited amount of air drying to create a substantially knot-free fluff. The fibers have imparted thereto an enhanced degree of curl relative to the amount of curl naturally present in such fibers. It is believed that this additional curl enhances the resilient character of structures made from the modified fibers herein. Other applicable methods of defibration include, but are not limited to, treatment in a Waring blender, tangentially contacting the fibers with a wire brush, and hammermilling. Preferably, an air stream is directed toward the fibers during such defibration to aid in separating the fibers into substantially individual form. Regardless of the particular mechanical device used, the fibers are mechanically treated while initially at a consistency of at least 40%. Defibrating at less than 40% consistency can foster formation of clumps of fibers. Preferably, defibrating is carried out on fibers at a consistency ranging from 50 to 70%. The defibrating can be carried out even on fibers of 100% consistency. However, defibrating at consistencies exceeding 80% can cause fiber damage, detracting from performance.

We turn now to step (c) of the method of the third embodiment herein, i.e., to the step of heating the product of step (b) in air at atmospheric pressure to remove any moisture content and to heat treat the resulting moisture-free high lignin content cellulosic fibers for at least 5 seconds.

As indicated above, this step may be carried out in two stages, a first drying stage (e.g., flash drying) to obtain a consistency of at least 60% if this consistency is not already present or to increase the consistency if a consistency of at least 60% is already present, e.g., to 85–95% or even 100% consistency, and a second stage to remove any remaining moisture content and heat treat the moisture-free high lignin content cellulosic fibers, e.g., by heating for 5 seconds to 2 hours at 120° C. to 280° C. (air temperature in the heating apparatus), preferably for 2 to 75 minutes at 150° C. to 190° C. (air temperature in the heating apparatus). If the fibers introduced into step (c) are at 100% consistency, the first stage is omitted.

The first stage is preferably carried out by a method known in the art as flash drying. This is carried out by transporting the defibrated fibers in a hot air stream at an introductory air temperature ranging from 200° to 750° F., preferably at an introductory air temperature ranging from 300° to 550° F., until the target consistency is reached. This imparts additional curl to the fibers as water is removed from them. While the amount of water removed by this drying step may be varied, it is believed that flash drying to the higher consistencies in the 60% to 100% range provides a greater level of fiber curl than does flash drying to a consistency in the low part of the 60%–100% range. In the preferred embodiments, the fibers are dried to about 85%–95% consistency. Flash drying the fibers to a consistency, such as 85%–95%, in a higher portion of the 60%–100% range, reduces the amount of drying which must be accomplished in the second stage.

We turn now to the second stage, wherein any remaining moisture content is removed and the moisture-free high lignin content cellulosic fibers are heat treated for at least 5 seconds. As indicated above, this stage may be carried out by heating for 5 seconds to 2 hours at 120° C. to 280° C. (air temperature in the heating apparatus). If more than a minimal amount of moisture is present, e.g., more than about 1% moisture, heating must be carried out for more than 5 seconds to obtain the required at least 5 second heat treatment, e.g., for at least 1 minute. In a preferred process, the second stage is carried out on a dried product of step (b) initially having a consistency ranging from 85 to 95% and the heating in the second stage is carried out for 2 to 75 minutes at 150° to 190° C. (air temperature in the heating apparatus) to remove any moisture content and heat treat the resulting moisture-free high lignin content cellulosic fibers for at least 1 minute. If the fibers treated in the second stage are not initially present in the second stage at a consistency of at least 60%, the removal of water to provide moisture-free fibers normally cannot be obtained so the limitation of heat treating moisture-free fibers, which allows obtaining appropriately stiffened fibers suitable for producing high bulk, highly porous structures, at atmospheric pressure and without use of a non-oxidizing atmosphere, is not realized. The second stage is readily carried out in a continuous air-through heating apparatus (heated air is passed perpendicularly through a traveling bed of fibers) or in a static oven (fibers and air are maintained stationary in a container housing a stationary heating means). The second stage may also be carried out by routing the effluent from a flash dryer of the first stage (at 90 to 100% consistency) to a cyclone separator which separates air from the air/fiber admixture from the flash drier, discharging the fibers from the cyclone separator into a stream of hot air (e.g., 400° F.) in a duct containing at least one U-shaped portion, which carries the fibers through the duct thereby providing a travel path which provides sufficient residence time to cause removal of any moisture content and the required heat treating, and discharging from the duct into a cyclone separator to separate the heat treated fibers, and if appropriate, carrying out additional heat treating, e.g., in a subsequent air-through oven or static oven. Apparatus for the flash drying of the first stage may also be the same kind of apparatus, i.e., an inlet side cyclone separator, hot air treatment duct and cyclone separator, so that two or more sets of such apparatus are used in series as required by the need to bring in fresh air over the course of drying and heat treating.

We turn now to the method of the fourth embodiment which comprises the step of heating a dry (0–40% moisture content) sheet of high lignin content fibers in air at atmospheric pressure to remove any moisture content and heat treat the moisture-free high lignin content cellulosic fibers for at least 5 seconds, e.g., the step of heating for 5 seconds to 2 hours at 120° C. to 280° C. (air temperature in the heating apparatus).

The starting material for the method of the fourth embodiment can be, for example, a sheet of fibers obtained commercially, e.g., high lignin content drylap, preferably Northern softwood chemithermomechanical drylap, which normally contains less than about 10% moisture (e.g., 0–10% moisture). If desired, the drylap or other kind of sheeted fibers may be moisture adjusted and/or pH adjusted, e.g., by transporting the sheet of fibers through a body of aqueous composition comprising water, contained in the nip of nip rolls (e.g., rolls 1 foot in diameter and 6 feet wide) and through said nip to produce on the outlet side of the nip an impregnated sheet of fibers containing the aqueous composition in an amount providing a consistency of 30 to 80% or more (e.g., even up to 85% or 90% or even 95%), preferably a consistency of 60 to 80%. In a less preferred alternative, the sheet of fibers is impregnated with aqueous composition to adjust the moisture content and/or pH by spraying. In either case, if the consistency is less than 60%, liquid removal is carried out to raise the consistency to at least this level, e.g., by dewatering (i.e., mechanically removing liquid, e.g., by centrifuging or pressing) and/or by drying under conditions such that utilization of high temperature for an extended period of time is not required, e.g., by a method known in the art as air drying. For example, a sheet of fibers at a moisture content of 6% can be passed through the body of aqueous composition and nip rolls to produce an impregnated sheet of fibers of 60% consistency or 80% consistency which is ready for treatment in the heating step of the fourth embodiment or to produce an impregnated sheet of fibers of a consistency of 40% which is subjected to a liquid removal step or steps as described above, e.g., to provide a consistency of 60%, before treatment in the heating step of the fourth embodiment.

If more than a minimal amount of moisture is present in the starting material sheet for the heating step for the fourth embodiment, heating must be carried out for more than 5 seconds to obtain the required at least 5 second heat treatment, e.g., for at least 1 minute.

In a preferred heating step of the fourth embodiment, a sheet of high lignin content cellulosic fibers at a consistency of 85–100% is heated for 2 minutes to 75 minutes at 150° C. to 190° C. (air temperature in the heating apparatus) to remove any moisture content and heat treat the moisture-free high lignin content fibers for at least 1 minute.

The heating step of the fourth embodiment is readily carried out in an air-through heating apparatus as described above or a static oven as described above.

The resulting heat treated sheet of fibers is preferably subjected to defibration by any of the methods of defibration described hereinbefore to produce fibers in unrestrained form. The heat treated sheet of fibers is preferably moisturized to 40 to 80% consistency, e.g., by spraying or by passing through a body of water in the nip for nip rolls, for the defibration.

The heating steps in the methods of the third and fourth embodiments should be such that the temperature of the fibers does not exceed about 227° C. (440° F.) since the fibers can burst into flame at this temperature.

Dry fibers resulting from the methods of the third and fourth embodiments are optionally moisturized, e.g., by spraying with water to provide a 5 to 15% moisture content. This makes the fibers resistant to damage that is of risk to occur due to subsequent handling or due to processing to make absorbent structures from the fibers.

We turn now to the uses of the heat-treated-in-air high lignin content cellulosic fibers herein.

The heat-treated-in-air high lignin content cellulosic fibers find application in production of a variety of absorbent structures including, but not limited to, paper towels, tissue sheets, disposable diapers, catamenials, sanitary napkins, tampons, and bandages wherein each of said articles has an absorbent structure containing said fibers. For example, a disposable diaper or similar article having a liquid permeable topsheet, a liquid impermeable backsheet connected to the topsheet, and an absorbent structure containing the heat-treated-in-air high lignin content cellulosic fibers herein is particularly contemplated. Such articles are described generally in U.S. Pat. No. 3,860,003, issued to Kenneth B. Buell on Jan. 14, 1975, hereby incorporated by reference into this disclosure.

The fibers herein may be utilized directly in the manufacture of air laid absorbent cores. Additionally, due to their stiffened and resilient character, the fibers herein may be wet laid into an uncompacted, low density sheet which, when subsequently dried, is directly useful without further mechanical processing as an absorbent core. The fibers herein may also be wet laid as compacted pulp sheets for sale or transport to distant locations.

Relative to pulp sheets made from conventional cellulosic fibers, the pulp sheets made from the fibers herein are more difficult to compress to conventional pulp sheet densities. Therefore, it may be desirable to combine the fibers herein with conventional fibers, such as those conventionally used in the manufacture of absorbent cores. Pulp sheets containing the fibers herein preferably contain between about 5% and about 90% unstiffened cellulosic fibers, based upon the total dry weight of the sheet, mixed with the fibers herein. It is especially preferred to include between about 5% and about 30% of highly refined, unstiffened cellulosic fibers, based upon the total dry weight of the sheet. Such highly refined fibers are refined or beaten to a freeness level less than about 300 ml CSF, and preferably less than 100 ml CSF. The unstiffened fibers are preferably mixed with an aqueous slurry of the fibers herein. This mixture may then be formed into a densified pulp sheet for subsequent defibration and formation into absorbent pads. The incorporation of the unstiffened fibers eases compression of the pulp sheet into a densified form, while imparting a surprisingly small loss in absorbency to the subsequently formed absorbent pads. The unstiffened fibers additionally increase the tensile strength of the pulp sheet and of absorbent pads made either from the pulp sheet or directly from the mixture of the fibers herein and unstiffened fibers. Regardless of whether the blend of the fibers herein and unstiffened fibers are first made into a pulp sheet and then formed into an absorbent pad or formed directly into an absorbent pad, the absorbent pad may be air-laid or wet-laid.

Sheets or webs made from the fibers herein, or from mixtures also containing unstiffened fibers, will preferably have basis weights of less than about 800 g/m$^2$ and densities of less than about 0.60 g/cm$^3$. Although it is not intended to limit the scope of the invention, wet-laid sheets having basis weights between 300 g/m$^2$ and about 600 g/m$^2$ and densities between 0.07 g/cm$^3$ and about 0.30 g/cm$^3$ are especially contemplated for direct application as absorbent cores in disposable articles such as diapers, tampons, and other catamenial products. Structures having basis weights and densities higher than these levels are believed to be most useful for subsequent comminution and air-laying or wet-laying to form a lower density and basis weight structure which is more useful for absorbent applications, Such higher basis weight and density structures also exhibit surprisingly high absorptivity and responsiveness to wetting. Other absorbent structure applications contemplated for the fibers herein include low density tissue sheets having densities which may be less than about 0.03 g/cc.

In one application to absorbent structures, the fibers herein are formed into either an air laid or wet laid (and subsequently dried) absorbent core which is compressed to pad form to a dry density less than the equilibrium wet density of the pad. The equilibrium wet density is the density of the pad, calculated on a dry fiber basis when the pad is fully saturated with fluid. When fibers are formed into an absorbent core having a dry density less than the equilibrium wet density, upon wetting to saturation, the core will collapse to the equilibrium wet density. Alternatively, when fibers are formed into an absorbent core having a dry density greater than the equilibrium wet density, upon wetting to saturation, the core will expand to the equilibrium wet density. Pads made from the fibers herein have equilibrium wet densities which are substantially lower than pads made from conventional fluffed fibers. The fibers herein can be compressed to a density higher than the equilibrium wet density, to form a thin pad which, upon wetting, will expand, thereby increasing absorbent capacity, to a degree significantly greater than obtained for unstiffened fibers.

Absorbent structures can also be made from admixtures of the fibers herein and cellulosic fibers stiffened with crosslinking agents such as those that are the subject of the concurrently filed patent application of Naieni and Herron mentioned above.

Absorbent structures made from the fibers herein may additionally contain discrete particles of substantially water-insoluble, hydrogel-forming materials. Hydrogel-forming materials are chemical compounds capable of absorbing fluids and retaining them under moderate pressures.

Suitable hydrogel-forming materials can be inorganic materials such as silica gels or organic compounds such as crosslinked polymers. Crosslinked hydrogel-forming polymers may be crosslinked by covalent, ionic, Van der Waals, or hydrogen bonding. Examples of hydrogel-forming materials include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogel-forming materials are those disclosed in Assarsson et al, U.S. Pat. No. 3,901,236, issued Aug. 26, 1975, the disclosure of which is incorporated herein by reference. Particularly preferred hydrogel-forming polymers for use in an absorbent core herein are hydrolyzed acrylonitrile grafted starch, acrylic acid grafted starch, polyacrylates, and isobutylene maleic anhydride copolymers, or mixtures thereof, Examples of hydrogel-forming materials which may be used are Aqualic L-73, a partially neutralized polyacrylic acid made by Nippon Shokubai Co., Japan, and Sanwet IM 1000, a partially neutralized polyacrylic acid grafted starch made by Sanyo Co., Ltd., Japan. Hydrogel-forming materials having relatively high gel strengths, as described in U.S. Pat. No. 4,654,039, issued Mar. 31, 1987, hereby incorporated herein by reference, are preferred for utilization with the fibers herein.

Process for preparing hydrogel-forming materials are disclosed in Masuda et al, U.S. Pat. No. 4,076,663, issued Feb. 28, 1978; in Tsubakimoto et al, U.S. Pat. No. 4,286,082, issued Aug. 25, 1981; and further in U.S. Pat. Nos. 3,734, 876, 3,661,815, 3,670,731, 3,664,343, 3,783,871, and Belgian Patent 785,850, the disclosures of which are all incorporated herein by reference.

The hydrogel-forming material may be distributed throughout an absorbent structure containing the fibers herein, or be limited to distribution throughout a particular layer or section of the absorbent structure. In another embodiment, the hydrogel-forming material is adhered or laminated onto a sheet or film which is juxtaposed against a fibrous, absorbent structure, which may include the fibers herein. Such sheet or film may be multilayered such that the hydrogel-forming material is contained between the layers. In another embodiment, the hydrogel-forming material may be adhered directly onto the surface fibers of the absorbent structure.

An important advantage has been observed with respect to absorbent structures made from the fibers herein having dry densities which are higher than their corresponding equilibrium wet densities (calculated on a dry fiber basis). Specifically, this type of absorbent structure expands in volume upon wetting. As a result of this expansion, the interfiber capillary network of fibers also enlarges. In conventional absorbent structures having hydrogel-forming material blended therein, the hydrogel-forming material expands in volume due to fluid absorption, and may block or reduce in size the capillary routes for fluid absorption prior to utilization of the entire fluid absorbing potential of the structure. This phenomenon is known as gel blocking. Capillary enlargement due to expansion of fibrous network of absorbent structure utilizing the fibers herein reduces the occurrence of gel blocking. This allows larger proportions of the fluid absorbency potential of the structure to be utilized and allows higher levels of hydrogel-forming material (if desired) to be incorporated into the absorbent structure, without significant levels of gel-blocking.

Absorbent structures containing the fibers herein and hydrogel-forming material for diaper core applications preferably have dry densities of between about 0.15 g/cc and about 0.40 g/cc and preferably contain less than about 20% hydrogel-forming material, calculated on a dry fiber weight basis.

The hydrogel-forming material may be homogeneously dispersed throughout all or part of the absorbent structure. For a diaper structure as disclosed in U.S. Pat. No. 3,860,003 having an absorbent core which contains the fibers herein, has a dry density of about 0.20 g/cc, and also contains hydrogel-forming material dispersed throughout the core, it is presently believed that an optimal balance of diaper wicking, total absorbent capacity, skin wetness, and economic viability is obtained for contents of between about 5 wt. % and about 20 wt. %, based on the total weight of the dry absorbent core, of a hydrogen forming material such as Aqualic L-73. Between about 8 wt. % and about 10 wt. % of hydrogel-forming material is preferably homogeneously blended with the fiber-herein-containing absorbent cores in products as disclosed in U.S. Pat. No. 3,860,003.

The absorbent structures described above may also include conventional, fluffed fibers, or highly refined fibers, wherein the amount of hydrogel-forming material is based upon the total weight of the fibers as previously discussed. The embodiments disclosed herein are exemplary in nature and are not meant to limited the scope of ampliation of hydrogel-forming materials with individualized, esterified fibers.

The invention herein is illustrated by the following specific examples.

In the reference example and examples hereinafter, results are evaluated in terms of WRV, 5K density, drip capacity, and wet compressibility.

Reference Example I

Drylap sheets of market Northern softwood chemithermomechanical pulp (CTMP) fibers (Sphinx), having about 20% lignin content, were dispersed by dipping and mixing with a paddle wheel mixer in a solution of citric acid and water at pH of 3.0 to yield a 10% consistency mixture. This mixture was centrifuged to provide a dewatered cake of approximate consistency of 50%. The dewatered cake, containing 6% citric acid on a fiber basis, was air dried to about 60% consistency, fluffed in a lab disc refiner and flash dried to about 90% consistency. Testing indicated a WRV of 131, a 5K density of 0.235 g/cc, a drip capacity of 5.9 g/g, and a wet compressibility at of 7.0 cc/g.

Example I

Drylap sheets of market chemithermomechanical pulp (CTMP) fibers (Sphinx), having about 20% lignin content, were dispersed by dipping and mixing with a paddle wheel mixer in water at pH of 8.9 to yield a 10% consistency mixture. This mixture was centrifuged to provide a dewatered cake of approximate consistency of 50%. The dewatered cake was air dried to about 60% consistency, fluffed in a lab disc refiner, flash dried to about 90% consistency and heated in a lab oven at an air temperature of 165° C. for 60 minutes. Testing indicated a 5K density of 0.158 g/cc, a drip capacity of 5.9 g/g, and a wet compressibility of 7.3 cc/g.

Example II

Example I was repeated except that the pH of the water was adjusted to 6.5 using sulfuric acid. Testing indicated a WRV of 120, a 5K density of 0.178 g/cc, a drip capacity of 7.6 g/g, and a wet compressibility of 7.9 cc/g.

Example III

Example I was repeated except that the pH of the water was adjusted to 3.0 using sulfuric acid. Testing indicated a 5K density of 0.135 g/cc, a drip capacity of 6.4 g/g, and a wet compressibility of 8.0 cc/g.

Example IV

Drylap sheets of market chemithermomechanical pulp fibers (Sphinx), having about 20% lignin content, and a moisture content of 6%, are heated in an air-through oven for 6 minutes at an air temperature of 350° F. The resulting sheet is defibrated using a disc refiner. The resulting fibers have significantly improved 5K density.

Example V

A drylap sheet of market chemithermomechanical pulp fibers (Sphinx) is processed as in Example IV except that the sheet is transported through a body of aqueous composition (pH adjusted to 6.5 with sulfuric acid) in the nips of nip rolls (the rolls are one foot in diameter by 6 feet wide) and through the nip rolls to produce on the output side of the nip an impregnated sheet of fibers of 80% consistency (residence time in the aqueous composition of 0.1 second) and are heated in the air-through oven for 20 minutes at air temperature of 350° F. The resulting sheet is moisturized to 20% moisture content by spraying with water and then is defibrated using a disc refiner. The resulting fibers have significantly improved 5K density, wet compressibility and drip capacity.

Example VI

Heat treated fibers prepared as in any of Examples I–V are air laid into absorbent pads, and compressed with a hydraulic press to a density of about 0.1 g/cc with a basis weight of about 0.13 g/in². The pads are cut to 15" by 3" for use as absorbent pads for sanitary napkins.

Variations will be obvious to those skilled in the art. Therefore, the invention is defined by the scope of the claims.

What is claimed is:

1. A method of preparing heat-treated-in-air high cellulosic fibers having at least about 10.0 wt. % lignin content on a dry basis which are free of moieties from crosslinking agents and have a water retention value ranging from 90 to 135 and a dry resiliency defined by a 5K density ranging from 0.08 to 0.20 g/cc, said method comprising the steps of:
  (a) providing high lignin content cellulosic fibers at a consistency of 40 to 80%, which are free of admixture with crosslinking agent;
  (b) subjecting the fibers to defibration,
  (c) heating said high lignin content cellulosic fibers in air at atmospheric pressure to remove any moisture content and heat treating the resulting moisture-free high lignin content cellulosic fibers at a temperature of between about 120° C. to about 280° C. for at least 5 seconds.

2. The method of claim 1 wherein the heating is carried out for 5 seconds to 2 hours at an air temperature of 120° C. to 280° C.

3. The method of claim 2 wherein the admixture of step (a) has a consistency ranging from 50 to 70%, and step (c) comprises flash drying to a consistency ranging from 85 to 95% and then heating for 2 to 75 minutes at an air temperature of 150° to 190° C. to remove the remaining moisture content and heat treat the resulting moisture-free high lignin content cellulosic fibers for at least 1 minute.

4. The method of claim 3 wherein the resulting high lignin content fibers are moisturized to provide a 5 to 15% moisture content.

5. A method of preparing heat-treated-in-air high lignin content cellulosic fibers which contain at least about 10.0 wt. % lignin on a dry basis are free of moieties from crosslinking agents and have a water retention value ranging from 90 to 135 and a dry resiliency defined by a 5K density ranging from 0.08 to 0.20 g/cc, said method comprising the step of heating a sheet of high lignin content cellulosic fibers of moisture content ranging from 0 to 40% in air at atmospheric pressure to remove any moisture content and heat treating the moisture-free high lignin content cellulosic fibers at a temperature of between about 120° C. to about 280° C. for at least 5 seconds.

6. The method of claim 5 wherein the heat treated sheet is subjected to defibrating.

7. The method of claim 6 wherein the heating is carried out for 5 seconds to 2 hours at an air temperature of 120° C. to 280° C.

8. The method of claim 7 wherein the heating is carried out for 2 minutes to 75 minutes at an air temperature of 150° C. to 190° C. to remove any moisture content and heat treat the moisture-free high lignin content fibers for at least 1 minute.

9. The method of claim 5 wherein the resulting high lignin content fibers are moisturized to provide a 5 to 15% moisture content.

* * * * *